US012678048B2

(12) United States Patent
Müller et al.

(10) Patent No.: US 12,678,048 B2
(45) Date of Patent: Jul. 14, 2026

(54) ARRANGEMENT FOR OPERATING A BIOSENSOR AND ARRANGEMENT FOR DETERMINING THE GLUCOSE CONTENT IN THE BLOOD

(71) Applicant: EYESENSE GMBH, Großostheim (DE)

(72) Inventors: Ralf Müller, Mittweida (DE); Achim Müller, Großostheim (DE); Roland Krivanék, Aschaffenburg (DE)

(73) Assignee: EYESENSE GMBH, Großostheim (DE)

( * ) Notice: Subject to any disclaimer, the term of this patent is extended or adjusted under 35 U.S.C. 154(b) by 914 days.

(21) Appl. No.: 17/782,397

(22) PCT Filed: Dec. 4, 2020

(86) PCT No.: PCT/EP2020/084747
§ 371 (c)(1),
(2) Date: Jun. 3, 2022

(87) PCT Pub. No.: WO2021/110977
PCT Pub. Date: Jun. 10, 2021

(65) Prior Publication Data
US 2023/0011856 A1     Jan. 12, 2023

(30) Foreign Application Priority Data

Dec. 6, 2019     (DE) ..................... 10 2019 133 365.2

(51) Int. Cl.
A61B 5/00          (2006.01)
A61B 5/145         (2006.01)
G01N 21/64         (2006.01)

(52) U.S. Cl.
CPC ........ A61B 5/0071 (2013.01); A61B 5/14532 (2013.01); G01N 21/645 (2013.01); *G01N 2021/6484* (2013.01)

(58) Field of Classification Search
CPC . A61B 5/0071; A61B 5/14532; A61B 5/0031; A61B 5/14865; A61B 5/6852; G01N 21/645; G01N 2021/6484; G01N 2021/6471; G01N 2021/772; G01N 2021/7786
See application file for complete search history.

(56) References Cited

U.S. PATENT DOCUMENTS 4,344,438 A     8/1982   Schultz
4,443,055 A *   4/1984   Matsuoka ............ G02B 26/125
                                            359/218.1

(Continued)

FOREIGN PATENT DOCUMENTS

DE     4322734 A1     1/1995
DE     4341086 A1 *   6/1995   ........... G02B 6/2852

(Continued)

OTHER PUBLICATIONS

Achim Josef Müller, et al. First Clinical Evaluation of a New Percutaneous Optical Fiber Glucose Sensor for Journal of Diabetes Science and Technology vol. 7, Issue 1, Jan. 2013.

*Primary Examiner* — Patrick Fernandes
*Assistant Examiner* — Shawn Curtis Broughton
(74) *Attorney, Agent, or Firm* — Kaplan Breyer Schwarz LLP

(57) ABSTRACT

An arrangement for operating a biosensor emitting radiation includes an excitation light source, which generates at least one excitation radiation for the biosensor; a coupling fiber, at the entry surface of which the excitation radiation is coupled in; an optical Y-coupler, including an excitation arm, which is connected to the exit surface of the coupling fiber, a detector arm, which is connected to an optical detector, and a sensor foot, which can be connected to the (Continued)

biosensor. The excitation arm has a conical shape. The radiation axis of the excitation arm includes an angle in the range of 5° to 70° with the main radiation axis of the detector arm. The diameter of the excitation arm at the connecting point to the detector arm is less than two thirds the diameter of the detector arm. An arrangement for determining the glucose content blood is also provided.

18 Claims, 3 Drawing Sheets

(56)                    References Cited

U.S. PATENT DOCUMENTS

| | | | |
|---|---|---|---|
| 4,496,211 A | 1/1985 | Daniel |
| 5,341,805 A | 8/1994 | Stavridi |

| | | | | |
|---|---|---|---|---|
| 5,999,673 A | * | 12/1999 | Valentin | G02B 6/2835 |
| | | | | 385/43 |
| 6,553,164 B1 | | 4/2003 | Ono | |
| 7,496,245 B2 | * | 2/2009 | Saaski | G02B 6/4206 |
| | | | | 385/12 |
| 2004/0072358 A1 | * | 4/2004 | Ballerstadt | A61B 5/1459 |
| | | | | 436/95 |
| 2008/0188725 A1 | | 8/2008 | Markle | |

FOREIGN PATENT DOCUMENTS

| | | | | |
|---|---|---|---|---|
| DE | 694 08 976 T2 | 7/1998 | | |
| DE | 69414139 T2 | 6/1999 | | |
| DE | 10 2015 101 847 B4 | 8/2016 | | |
| EP | 2 989 975 A1 | 3/2016 | | |
| WO | WO-2013033076 A1 * | 3/2013 | | A61B 5/742 |
| WO | 2014/116597 A1 | 7/2014 | | |

* cited by examiner

ARRANGEMENT FOR OPERATING A BIOSENSOR AND ARRANGEMENT FOR DETERMINING THE GLUCOSE CONTENT IN THE BLOOD

BACKGROUND OF THE INVENTION

The present invention relates to a fiber optic arrangement for operating a biosensor. The biosensor is in particular, though not exclusively, suitable for determining the glucose content of blood. The invention thus also relates to an arrangement for determining the glucose content of blood.

Optical sensors are used, among other things, for the evaluation of fluorescent radiation. In many cases, an optical arrangement both provides excitation radiation and evaluates the radiation emitted by a suitable luminophore. The intensity of the emitted fluorescent radiation can be a measure of a variable to be monitored.

For example, DE 10 2015 101 847 B4 describes an arrangement for examining a sample that can be excited by means of electromagnetic radiation. To separate the excitation radiation from the emitted measuring radiation, the arrangement includes a first dichroic beam splitter comprising a first prism and a second prism, which are connected to one another at the base surfaces thereof, and including a dichroic layer arranged between the base surfaces of the two prisms. A light source provides electromagnetic radiation suitable for exciting the sample, which is coupled into the entry surface of the first prism. Part of the radiation is reflected at the dichroic layer in the direction of the sample, which is positioned downstream from an exit surface of the first prism. A detector is used to detect the electromagnetic measuring radiation that is emitted by the sample, passed through the beam splitter, and leaves the beam splitter at a measuring surface. A disadvantage of such arrangements is the sensitive and comparatively large design which, for example, makes it seemingly impossible to use them in day-to-day situations by untrained staff.

Muller A J, Knuth M, Nikolaus K S, Krivánek R, Küster F, Hasslacher C. "First clinical evaluation of a new percutaneous optical fiber glucose sensor for continuous glucose monitoring in diabetes." Journal of Diabetes Science and Technology 2013; 7(1):13-23. 2013 Jan. 1, describe an arrangement comprising a glucose-sensitive sensor designed as a biosensor at the end of an optical fiber. One or more fluorescent luminophores are arranged for this purpose at the fiber, which are excited by excitation radiation. The excitation radiation is supplied by an LED and is coupled into the fiber via a lens. In the specific application case, the intensity of the emitted fluorescent radiation is dependent on the glucose content of blood in tissue into which the fiber can be implanted. The emitted fluorescent radiation is guided in the fiber to and evaluated by a detector. In principle, such a biosensor is suitable for a quasi-continuous measurement of the blood sugar content, so that the supplied values can, for example, be fed to an insulin dosing unit to feed insulin to a patient as needed. However, feeding the excitation radiation and evaluating the fluorescent radiation supplied by the biosensor are technologically difficult to implement in very small units, so that the patient would be forced to carry a larger arrangement with him or her.

DE 694 08 976 T2 describes a glucose monitor containing a light source, a sensor and a processor. The light source emits excitation light that is directed at the sample to induce glucose in the sample to fluoresce. The excitation light causes the sample to produce return light, which includes fluorescent light produced by any glucose in the sample. The sensor monitors the return light and generates two signals representing the intensity of the light within two spectral wavelength bands. The first signal is indicative of the intensity of return light having a wavelength within a first wavelength band. The second signal is indicative of the intensity of light within a second wavelength band. The processor processes the two electrical signals to determine the concentration of glucose in the sample. Fibers or waveguides for guiding the light, a dichroic filter for separating the excitation light from the return light, a stop having a slit, and a prism are used as optical components.

U.S. Pat. No. 4,344,438 discloses a solution for measuring, in vivo, the concentration of low molecular weight plasma constituents. A fluorescence-based glucose sensor comprising a catheter measuring chamber is shown, wherein the detection device and the light source device are in optical contact with the chamber via optical fibers. The excitation light makes its way from the source, through a filter, to a half-silvered mirror, and is then focused onto the end of an optical fiber. In one embodiment, these components can be miniaturized by using an LED for the light source, and a photodiode for the light detector, and by implanting the whole arrangement into the body.

WO 2014/116597 A1 shows an optical system for detecting fluorescent light of a biological sample. An optical coupler that is used comprises a fiber for contacting a fluorescent body, a light-emitting diode, multiple filters, and a photodiode.

EP 2 989 975 A1 shows a fiber optic glucose sensor, comprising an element including proximal and distal end regions, wherein the proximal end region is configured for coupling to an optical device including an excitation light source and a detector. The distal end can be positioned in a blood vessel and comprises a cavity and a reflective surface, wherein the cavity comprises an indicator system.

DE 43 22 734 A1 and DE 43 41 086 A1 show an optical Y-coupler, composed of a continuous optical waveguide that has a polymer sheath, and an optical waveguide including a polymer sheath and entering from the side. The continuous optical waveguide extends in a straight manner at the point where it enters, and the optical waveguide that enters from the side extends at an angle α, which is smaller than the critical angle for the total reflection in the continuous optical waveguide. The continuous optical waveguide has a diameter of 50 to 6000 μm.

U.S. Pat. No. 6,553,164 shows a waveguide-based Y-coupler, which is composed of 4 individual sub-elements.

DE 694 14 139 T2 describes a coupling arrangement between a multi-mode light source and an optical fiber by means of an intermediate fiber, which is designed as an optical multi-mode intermediate fiber. The intermediate fiber comprises a sub-region having a cross-section and a tapering sub-region. A Y-coupler is designed by means of the tapering intermediate fiber.

US 2004/0072358 A1 describes a glucose detection device, which comprises a sensor, a light source and a photodetector, which are connected to one another by an optical fiber. Furthermore, a Y-coupler is utilized, which is formed by an optical fiber splitting into two strands.

Proceeding from US 2004-0072358 A1, it is an object of the present invention to provide an improved arrangement for operating a biosensor. The arrangement is intended both to supply the excitation radiation and to be able to detect the measurement signals generated by the sensor with high sensitivity. In the process, a small, integratable design, a secure mechanical connection to the biosensor and high optical reliability are to be achieved. In addition, it is considered to be an object to provide an improved arrangement for determining the glucose content, in particular in blood, which allows a mobile, quasi-continuous measurement of the glucose content.

SUMMARY OF THE INVENTION

These and other objects are achieved by an arrangement for operating a biosensor according to the appended claim 1, and by an arrangement for determining the glucose content according to claim 17.

The arrangement according to the invention for operating a biosensor includes an excitation light source, which generates at least one excitation radiation for the biosensor. The arrangement furthermore comprises a coupling fiber, at the entry surface of which the excitation radiation is coupled in. In addition, an optical Y-coupler is provided, which includes an excitation arm, which is connected to the exit surface of the coupling fiber, a detector arm, which is connected to an optical detector, and a sensor foot, which can be connected to the biosensor. The detector arm and the sensor foot preferably have a shared main radiation axis. The radiation axis of the excitation arm extends at an angle in the range of 5° to 70°, preferably 5° to 30°, with respect to the main radiation axis of the detector arm. The excitation arm has an elongated, conical shape, wherein the diameter of the excitation arm, at the entry point into the detector arm, is less than two thirds the diameter of the detector arm at this connecting point, preferably less than half, and particularly preferably less than one third of the diameter of the detector arm.

The excitation light source is preferably formed by an LED chip, which emits excitation radiation of 595 nm, for example. The excitation radiation is adapted to the biosensor in terms of the wavelength and optical power and can, for example, also contain two wavelengths if this is desired for the particular application purpose. The emission plane of the LED chip is preferably positioned at a distance of 0.1 to 10 times the diameter of the coupling fiber from the entry surface of the coupling fiber.

According to a preferred embodiment, the excitation light source is a planar, diffusely emitting emitter. The emission is preferably carried out from a thin layer, as is the case, for example, with a thin-film LED. The excitation light source is thus particularly preferably formed by a thin-film LED.

The coupling fiber is preferably a PMMA fiber or a sapphire fiber, which has a spherical, aspherical or planar entry surface, for example, which is located opposite the excitation light source. The coupling fiber preferably has a diameter that is constant across the length thereof and that is in the range of 0.1 to 2 mm, more preferably 0.3 to 0.7 mm, particularly preferably 0.5 mm, and a length that is preferably 7 times to 13 times the distance between the excitation light source and the entry surface of the coupling fiber, for example 5 to 15 mm, particularly preferably 10 mm. The entry surface of the coupling fiber is preferably spaced approximately 0.8 to 1.2 mm, particularly preferably approximately 1 mm, apart from the excitation light source, wherein the excitation beam preferably extends in air at this distance. This distance causes only "flat beams" to be coupled into the coupling fiber, which thus have only a small angle with respect to the central axis of the coupling fiber. The emitting surface of the excitation light source preferably corresponds to 10 to 60% of the cross-sectional surface of the coupling fiber.

An advantageous embodiment is characterized in that the coupling fiber does not have a curvature in the axial longitudinal direction, i.e., the longitudinal axis thereof extends rectilinearly. For example, the coupling fiber can be made of a rigid material for this purpose, or may be guided in a non-curved sleeve.

According to a preferred embodiment, the exit surface of the coupling fiber is coupled to the excitation arm of the optical Y-coupler by means of an interposed cut-off filter. As a result of this filter, the wavelengths that correspond to the fluorescence wavelengths emitted by the biosensor can be filtered out of the excitation radiation, so that these can be detected more easily at the detector as measurement signals. The cut-off filter is formed, for example, as a carrier glass including filter layers applied thereon. The exit surface of the coupling fiber can be glued to this carrier glass, wherein gluing directly onto the filter layers is also possible.

A particularly preferred embodiment is characterized by a specially adapted beam guidance, which allows optimized use of the available optical power. For this purpose, the aforementioned "flat beams" are coupled into the coupling fiber mentioned. "Flat beams" shall be understood to mean beams having a small angular deviation in the direction of propagation. The use of such beams above all allows the cut-off filter to be used efficiently, which already cuts certain wavelengths out of the excitation radiation, which then no longer distort the measurement result. The excitation radiation shall be sought to impinge as perpendicularly as possible on the surface of the cut-off filter, which is achieved when the excitation radiation propagates in the coupling fiber at the smallest possible angular deviation from the longitudinal axis of the coupling fiber, and thus impinges on the cut-off filter at the smallest possible angular deviation with respect to the surface perpendicular of the cut-off filter. The excitation radiation preferably extends in the coupling fiber at an angle of <40° with respect to the surface perpendicular of the cut-off filter or with respect to the core axis of the coupling fiber, particularly preferably at an angle of <30°, in particular <25°.

An advantageous embodiment of the arrangement is characterized in that the diameter of the excitation arm continuously decreases from the entry surface thereof, which is optically coupled to the exit surface of the coupling fiber, in the direction of the point at which it is connected to the detector arm (so-called tapered fiber). The excitation arm thus has the shape of an elongated frustum. At the connecting point, that is, at the position at which the excitation arm, the detector arm and the sensor foot of the Y-coupler converge, the diameter of the coupling arm is thus considerably smaller than at the entry surface thereof. The diameter of the excitation arm preferably decreases along the longitudinal extension thereof by more than half. In particular, the excitation arm has a diameter in the range of 0.1 to 0.2 mm at the point at which it connects to the detector arm. The tapering of the excitation arm serves primarily the formation of an optical valve, which allows the excitation radiation to be coupled into the sensor foot, while minimizing fluorescent radiation returned from the biosensor from undesirably exiting into the excitation arm.

According to a preferred embodiment, a colored glass piece, which enhances the filter action of the cut-off filter, is located between the coated carrier glass, which adjoins the exit surface of the coupling fiber, and the entry surface of the excitation arm. The colored glass piece is designed in the manner of a waveguide and can likewise have a conical shape. A colored glass piece is a colored, optical filter glass, such as is offered, for example, by Schott A G.

The Y-coupler is preferably made of plastic, and in particular PMMA or PC. For example, 3D printing methods or injection molding methods are suitable for this purpose. The diameters of the detector arm and of the sensor foot are preferably constant, for example in the range of 0.4 to 0.6 mm, and in particular 0.5 mm. The sensor foot can advantageously have a curvature having an angle of approximately 90° in the longitudinal direction, so as to be easily connectable at the exit surface thereof to the biosensor if the biosensor was implanted into the tissue substantially perpendicularly to a patient's skin surface.

An expedient embodiment includes a further colored glass piece in waveguide form, which is arranged between the detector and the exit surface of the detector arm. This colored glass piece, in turn, fulfills filter-enhancing functions. Furthermore, it is advantageous when a lens and a filter are arranged upstream from the detector so as to collimate the fluorescent radiation coming from the detector arm, and possibly filter out excitation radiation that is still present.

The detector can preferably be designed as a photodiode or as a similar component. If multiple fluorescence wavelengths are to be detected, it may be advantageous to combine a beam splitter with multiple photodetectors of varying sensitivities.

According to the invention, the sensor foot is not only used for the mechanical coupling to the sensor fiber, but also for the beam deflection. Preferably, a toric surface is formed in the sensor foot for this purpose.

An arrangement according to the invention for determining the glucose content, in particular of blood, comprises a biosensor as well as an arrangement for operating the same according to one of the embodiments described here.

BRIEF DESCRIPTION OF THE DRAWINGS

Further advantages and details of the invention will be apparent from the following description of preferred embodiments with reference to the drawings. In the drawings.

DETAILED DESCRIPTION OF THE INVENTION

Figure 1:
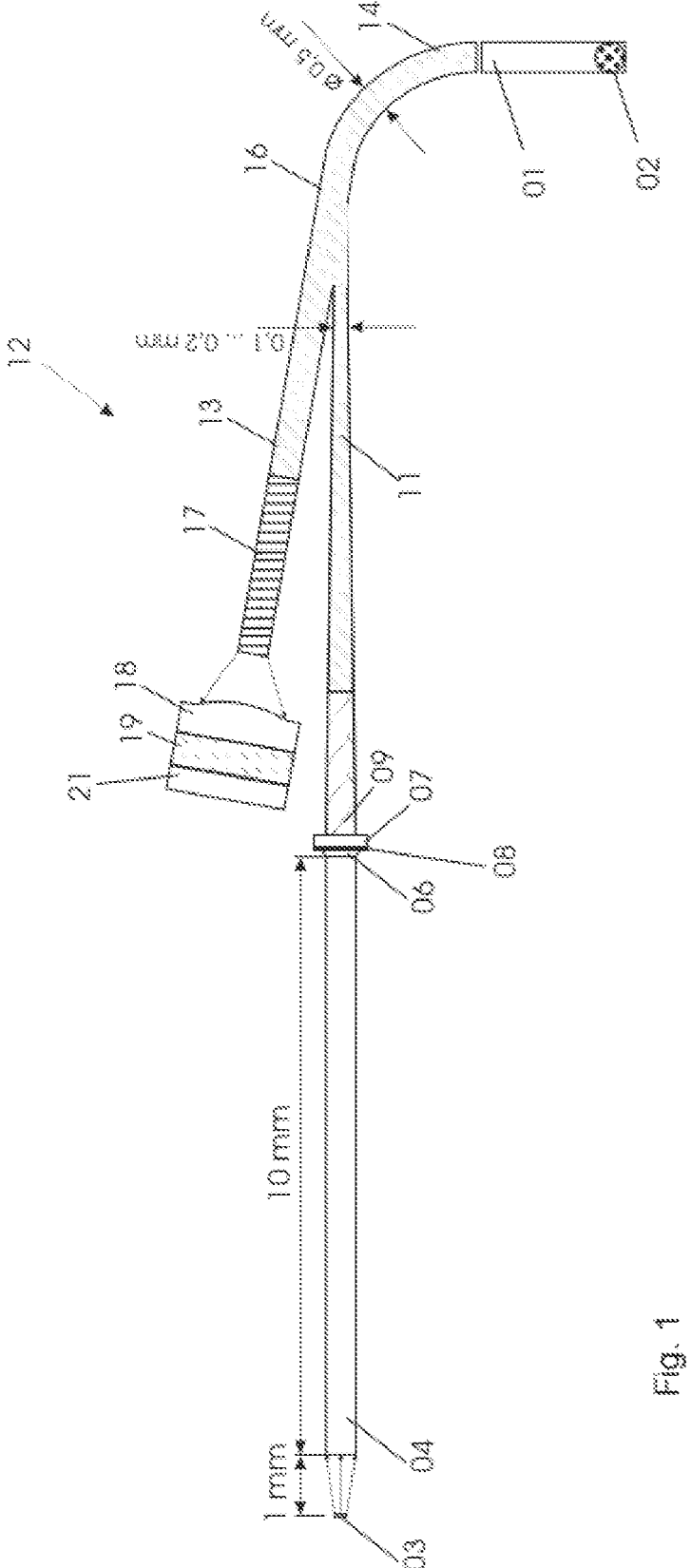
FIG. 1 shows a schematic diagram of a first embodiment of an arrangement according to the invention for operating a biosensor.

FIG. 1 shows an arrangement for operating a biosensor in a simplified lateral illustration. The biosensor is formed as a sensor fiber 01 here, which at the free end thereof is equipped with immobilized, glucose-sensitive fluorescent luminophores 02. Upon excitation by an excitation radiation, these fluorescent luminophores emit fluorescent radiation, the intensity of which is dependent on the glucose concentration in a medium in which the end of the biosensor is positioned. The medium can in particular be blood.

The arrangement for operating the biosensor includes an LED chip 03 as an excitation light source, preferably a thin-film LED. The LED chip 03 emits the excitation radiation and couples it at a flat angle into a coupling fiber 04. The angle between the excitation radiation and the core of the coupling fiber is preferably <30°. For this purpose, the LED 03 is positioned spaced approximately 1 mm apart from the entry surface of the coupling fiber 04 in the shown embodiment. The entry surface of the coupling fiber can be configured as a free-form, spherical, aspherical or planar surface. The coupling fiber 04 has a diameter of 0.5 mm and a length of 10 mm, for example. The exit surface of the coupling fiber 04 is attached to a carrier glass 07 by way of an adhesive 06. The carrier glass 07 is equipped with one or more filter layers 08 so as to act as a cut-off filter and to filter the wavelength of the fluorescent radiation that is emitted by the fluorescent luminophores 02 out of the excitation radiation. A first colored glass piece 09, which enhances the action of the cut-off filter, follows the carrier glass 07 in the propagation direction of the excitation radiation. The first colored glass piece 09 is configured in the form of a waveguide and, on the opposite side, adjoins an excitation arm 11 of an optical Y-coupler 12. The excitation arm 11 and the first colored glass piece 09 have a cross-section that tapers in the radiation direction. The diameter of the excitation arm 11 at the end thereof facing away from the coupling fiber 04 is thus only 0.1 to 0.2 mm, for example.

The Y-coupler 12 additionally includes a detector arm 13 and a sensor foot 14. At a connecting point 16, the excitation arm 11 joins the material that, otherwise, is continuous from the detector arm 13 to the sensor foot 14. At the connecting point 16, the detector arm 13 and the excitation arm 11 include an angle in the range of 5° to 70°, preferably 5° to 30°, and particularly preferably approximately 15°. The main radiation axes of the detector arm 13 and of the sensor foot 14 extend coaxially in the shown embodiment. In modified embodiments, the main radiation axes of the detector arm and of the sensor foot, however, can also extend at an angle with respect to one another, for example at a change in angle of 10° to 40°. The sensor foot 14 is configured to be flexible or curved at the end thereof facing away from the connecting point 16, so as to be able to be connected to the sensor fiber 01. The detector arm 13 and the sensor foot 14 have a diameter of 0.5 mm, for example.

The excitation radiation is guided from the LED chip 03 via the coupling fiber 04, the excitation arm 11 and the sensor foot 14 into the sensor fiber 01, where it excites the fluorescent luminophores 02. The fluorescent radiation emitted by the luminophores runs through the sensor fiber 01, back to the sensor foot 14 of the Y-coupler 12, and then, for the most part, into the detector arm 13. A second colored glass piece 17, which is formed in the form of a waveguide, adjoins the end of the detector arm 13 facing away from the connecting point 16. An optical lens 18 is provided for collimating the fluorescent radiation exiting at the exit surface of the second colored glass piece 17, which is followed by a further filter 19 so as to allow only the fluorescent radiation to pass to a downstream detector 21.

Figure 2:
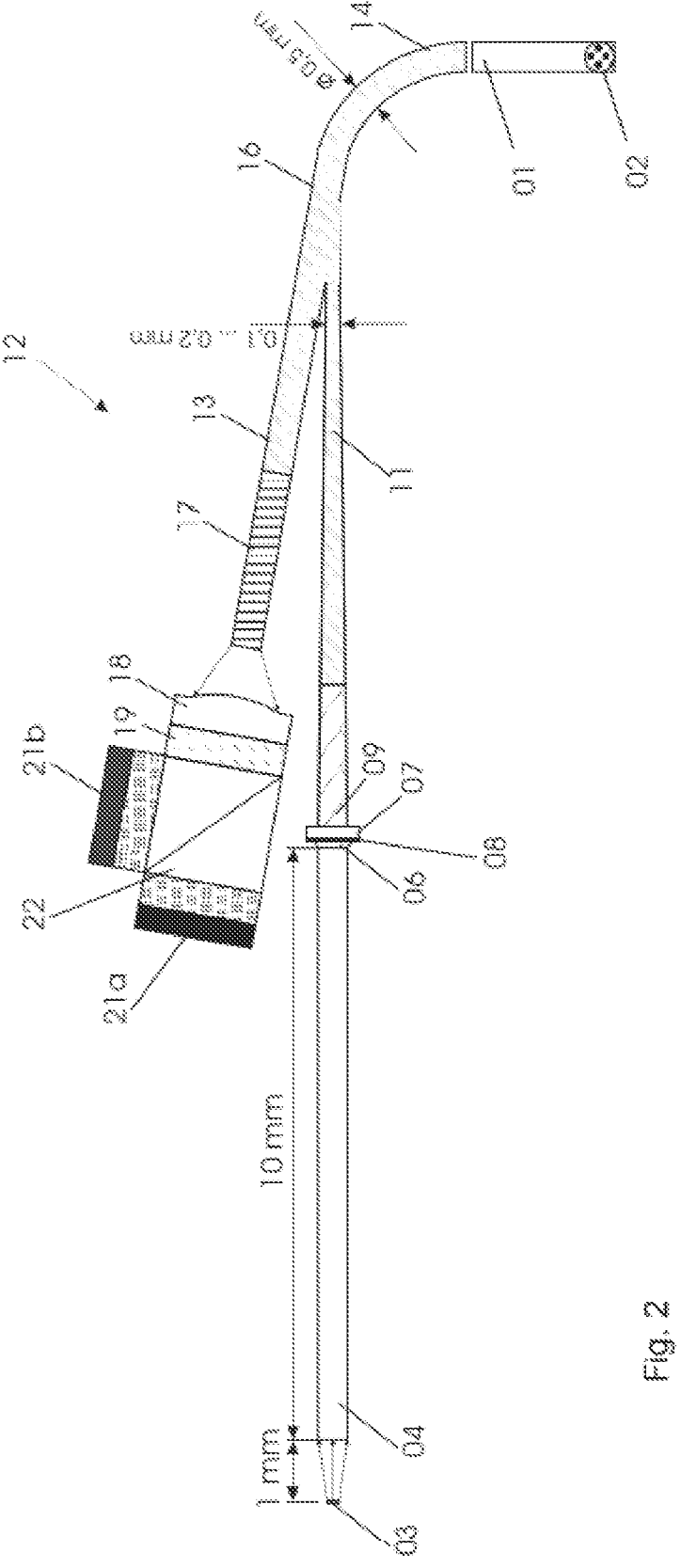
FIG. 2 shows a schematic diagram of a second embodiment of the arrangement for operating the biosensor.

FIG. 2 shows a modified embodiment of the arrangement for operating the biosensor, which initially largely agrees with the design according to FIG. 1. One difference is that the detector is divided into two sub-detectors 21a and 21b, which are used to detect different wavelengths of the fluorescent radiation. For this purpose, a beam splitter 22 is located downstream from the filter 19 in the radiation direction, which splits the fluorescent radiation into two sub-beams, as a function of the wavelength, which are then fed to the respective sub-detectors 21a, 21b. The second colored glass piece 17 enhances the action of the filter 19.

Figure 3:
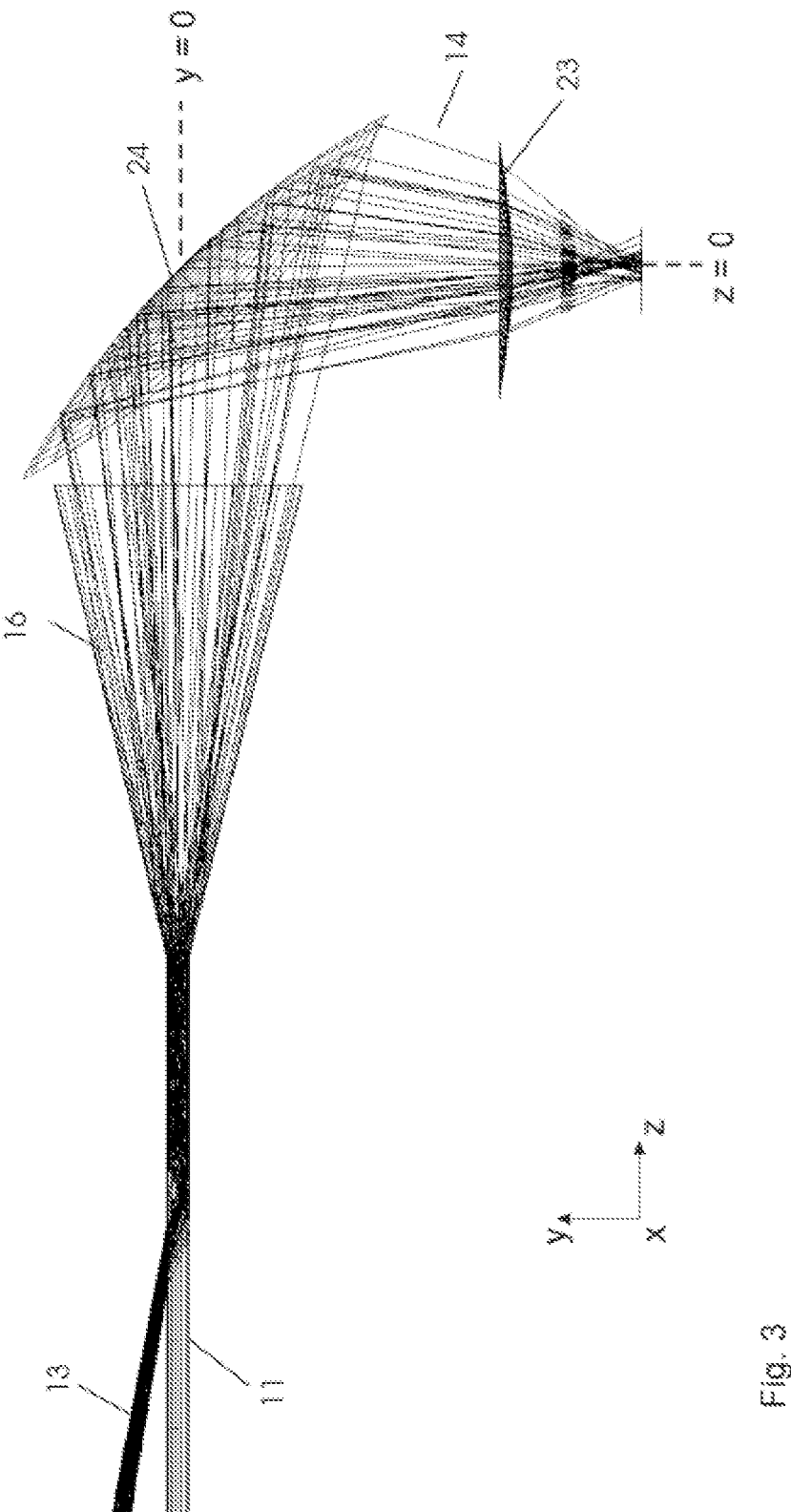
FIG. 3 shows an optical beam path in a sensor foot for beam deflection and for coupling into or outcoupling from the sensor fiber, with low optical losses.

FIG. 3 shows, by way of example, the optical beam path in the excitation arm 11, in the detector arm 13, in the region of the connecting point 16 and, above all, in the sensor foot 14. The sensor foot 14 is used for beam deflection and for coupling into or outcoupling from the sensor fiber, while creating the option of a distance of several 100 μm between the sensor foot and the sensor fiber, whereby the positioning is considerably simplified. As is already apparent from FIGS. 1 and 2, the sensor foot 14 is preferably configured to be curved or bent, so as to be easily connectable to the sensor fiber 01 and achieve a beam deflection. The entry surface at the excitation arm 11 and the exit surface at the sensor foot 14 are thus situated at an angle of more than 45°, and preferably of approximately 90°, with respect to one another. The connecting point 16 is particularly preferably optically configured in the manner of a funnel, as is illustrated by the beam path in FIG. 3.

The funnel-shaped configuration of the connecting point 16 also yields a major advantage for the optical return path, that is, the path of the fluorescent light that is guided from the sensor fiber 01 back to the detector 21. As a result of the shown beam guidance, the optical losses can be minimized, up to the point at which the excitation arm enters into the detector arm. The comparatively low emissions that originate from the fluorescent luminophores 02 can thus be evaluated particularly well at the detector. In this way, a distance of several 100 μm can be implemented between the sensor foot and the sensor fiber, which is of great advantage for designs relevant for practical applications.

A lens 23 is preferably formed on the side of the sensor foot 14 which faces the sensor fiber 01, and preferably is integrated into the material of the sensor foot. The lens 23 is situated downstream from the toric surface in the direction of the excitation radiation so as to focus the excitation radiation onto the input end face of the sensor fiber 01. The lens can be designed as a spherical or an aspherical lens, and can possibly be non-reflecting.

Particularly preferably, the numerical aperture that results downstream from the lens 23 at the sensor foot 14 in the direction of the sensor fiber 01 is adapted so as to substantially correspond to the numerical aperture of the sensor fiber.

According to a preferred embodiment, the diameter of the excitation arm 11 widens in the region of the connecting point 16, as is illustrated based on the beam path in FIG. 3. This widening preferably takes place by a linear, or alternatively by a non-linear, increase in the diameter in the direction of the sensor foot 14. The surface lines of the cone of the widening which results in the longitudinal section can thus be arbitrarily shaped.

In the region of the curvature of the sensor foot, the beams are deflected, preferably at a toric surface 24, which can be mathematically described as follows:

$$z = \frac{C * y^2}{1 + \sqrt{1 - (C^2 * (1 + CC) * y^2)}}$$

where
the first radius of the toric surface relates to the x axis (radius about an axis in the x direction) (R_about_x; C=1/R_about_x);
CC=conic constant;
the Y coordinate is inserted into the formula as y, yielding the Z coordinate in the case where the toric surface has its origin in point Y=0 and Z=0 and is not rotated counterclockwise by 45°; the second radius of the toric surface relates to the y axis (radius about the axis in the y direction) for the case where the toric surface is not rotated counterclockwise by 45°.

The reflection occurs at the toric surface, preferably as total reflection. For example, an additional reflecting layer can be applied in this region. This is expedient if the refractive index of the material in the sensor foot is too small, in which case total reflection is not possible. In this case, an additional reflecting layer can be provided on the toric surface.

This configuration ensures that the excitation radiation extends from the excitation arm 11, across the widening in the region of the connecting point 16 and the toric surface 24, to the lens 23, in the material of the excitation arm. A transition to air or gas, and then into the sensor fiber 01, does not occur until the lens 23.

The invention claimed is:

1. An arrangement for operating a biosensor emitting radiation, comprising:
an excitation light source, which generates at least one excitation radiation for the biosensor;
a coupling fiber, at the entry surface of which the excitation radiation is coupled in;
an optical detector; and
an optical Y-coupler, including an excitation arm, which is connected to an exit surface of the coupling fiber, a detector arm, which is connected to the optical detector, and a sensor foot configured to connect to the biosensor,
wherein the excitation arm has a conical shape, wherein the radiation axis of the excitation arm includes an angle in the range of 5° to 70° with the main radiation axis of the detector arm at a connecting point between the detector arm and the excitation arm, wherein a diameter of the excitation arm at the connecting point to the detector arm is less than two thirds a diameter of the detector arm, and wherein the excitation arm has a cross-section that tapers in a radiation direction, and
wherein the diameter of the excitation arm continuously decreases from an entry surface of the excitation arm to a connection point between the excitation arm and the detector arm, the excitation arm has a shape of an elongated frustum.

2. The arrangement according to claim 1, wherein the diameter of the excitation arm at the connecting point is less than half as large as at the entry surface thereof.

3. The arrangement according to claim 1, wherein the detector arm and the sensor foot have a shared main radiation axis.

4. The arrangement according to claim 1, wherein the excitation light source is an LED chip, the emission plane of which is positioned at a distance of 0.1 to 10 times a diameter of the coupling fiber from the entry surface of the coupling fiber.

5. The arrangement according to claim 4, wherein the coupling fiber has a length that is 7 times to 13 times the distance between the excitation light source and the entry surface of the coupling fiber.

6. The arrangement according to claim 4, wherein the entry surface of the coupling fiber is designed as a planar, spherical, aspherical or free-form surface.

7. The arrangement according to claim 1, wherein a cut-off filter, which filters the wavelength of the radiation emittable by the biosensor out of the excitation radiation, is arranged between the exit surface of the coupling fiber and the entry surface of the excitation arm.

8. The arrangement according to claim 1, wherein the coupling fiber is designed with a rectilinearly extending longitudinal axis.

9. The arrangement according to claim 7, wherein the cut-off filter is composed of a carrier glass including optical filter layers applied thereon.

10. The arrangement according to claim 7, wherein a colored glass piece in waveguide form is arranged between the carrier glass and the entry surface of the excitation arm.

11. The arrangement according to claim 1, wherein a lens is arranged between the exit surface of the detector arm and the detector for collimating the radiation emitted by the biosensor.

12. The arrangement according to claim 11, wherein an optical filter, which blocks incoming fractions of the excitation radiation, is arranged between the lens and the detector.

13. The arrangement according to claim 1, wherein a colored glass piece in waveguide form is arranged at the exit-side end of the detector arm.

14. The arrangement according to claim 1, wherein the excitation light source, the coupling fiber, the Y-coupler and the optical detector are integrated in a shared housing.

15. The arrangement according to claim 1, wherein the sensor foot comprises a curved section, in which a beam deflection is carried out at an angle of more than 45°.

16. The arrangement according to claim 15, wherein a beam-deflecting, toric surface is formed in the sensor foot.

17. An arrangement for determining a glucose content, in particular of blood, comprising:

a biosensor, which can be implanted into tissue and emits radiation upon excitation;

an excitation light source, which generates at least an excitation radiation for the biosensor;

a coupling fiber, at an entry surface of which the excitation radiation is coupled in;

an optical detector; and an optical Y-coupler including an excitation arm, which is connected to an exit surface of the coupling fiber, a detector arm, which is connected to the optical detector, and a sensor foot, which is connected to the biosensor, wherein the excitation arm has a conical shape, wherein the radiation axis of the excitation arm includes an angle in the range of 5° to 70° with the main radiation axis of the detector arm at a connecting point between the detector arm and the excitation arm, wherein a diameter of the excitation arm at the position of the connecting point to the detector arm is less than two thirds a diameter of the detector arm and wherein the excitation arm has a cross-section that tapers in a radiation direction, wherein the diameter of the excitation arm continuously decreases from an entry surface of the excitation arm to a connection point between the excitation arm and the detector arm, the excitation arm has a shape of an elongated frustum.

18. The arrangement according to claim 17, wherein the biosensor is formed as an optical fiber, which includes glucose-sensitive fluorescent luminophores at the exit surface thereof, which upon excitation by the excitation radiation emit fluorescent radiation having a fluorescent wavelength.

* * * * *